US011464919B2

(12) United States Patent
Bartels et al.

(10) Patent No.: US 11,464,919 B2
(45) Date of Patent: Oct. 11, 2022

(54) ATOMISER, IN PARTICULAR INHALER, FOR ATOMISING A LIQUID ACTIVE AGENT TO FORM AN AEROSOL AND A CORRESPONDING METHOD

(71) Applicant: SOFTHALE NV, Diepenbeek (BE)

(72) Inventors: Frank Bartels, Hattingen (DE); Jürgen Rawert, Cologne (DE)

(73) Assignee: SOFTHALE NV, Diepenbeek (BE)

( * ) Notice: Subject to any disclaimer, the term of this patent is extended or adjusted under 35 U.S.C. 154(b) by 805 days.

(21) Appl. No.: 16/338,083

(22) PCT Filed: Sep. 29, 2017

(86) PCT No.: PCT/EP2017/074775
§ 371 (c)(1),
(2) Date: Mar. 29, 2019

(87) PCT Pub. No.: WO2018/060425
PCT Pub. Date: Apr. 5, 2018

(65) Prior Publication Data
US 2020/0023145 A1    Jan. 23, 2020

(30) Foreign Application Priority Data
Sep. 30, 2016  (DE) .................... 10 2016 118 654.6

(51) Int. Cl.
*A61M 11/00*  (2006.01)
*A61M 15/00*  (2006.01)

(52) U.S. Cl.
CPC ...... *A61M 11/007* (2014.02); *A61M 15/0001* (2014.02); *A61M 15/0065* (2013.01); *A61M 11/00* (2013.01); *A61M 2202/0007* (2013.01)

(58) Field of Classification Search
CPC ............ A61M 11/007; A61M 15/0001; A61M 2202/0007; A61M 2202/0468;
(Continued)

(56) References Cited

U.S. PATENT DOCUMENTS 3,900,138 A * 8/1975 Phillips ............... A61M 15/009
239/338
5,497,944 A * 3/1996 Weston ................. B05B 9/0883
128/200.22
(Continued)

FOREIGN PATENT DOCUMENTS

EP            2234728 B1   10/2014
JP       1988-191276 U1   12/1988
(Continued)

OTHER PUBLICATIONS

English translation for JP1988-191276U1, human translated on Jan. 2022.*
(Continued)

*Primary Examiner* — Tu A Vo
(74) *Attorney, Agent, or Firm* — Hoxie & Associates LLC

(57) ABSTRACT

An atomiser, in particular an inhaler, for atomising a liquid active agent to form an aerosol, having, inter alia, an active agent reservoir, an atomiser nozzle and a pump arrangement, wherein a suction side of the pump arrangement leads into the active agent reservoir and a pressure side of the pump arrangement leads into the atomiser nozzle, and wherein the pump arrangement has a plunger that can be adjusted in a cylinder in the axial direction of the cylinder. A corresponding method is also described.

18 Claims, 6 Drawing Sheets

(58) Field of Classification Search
CPC .. A61M 15/0065; A61M 11/00; A61M 11/06; A61M 11/08
See application file for complete search history.

(56) References Cited

U.S. PATENT DOCUMENTS

| | | | |
|---|---|---|---|
| 5,662,271 | A | 9/1997 | Weston et al. |
| 7,104,470 | B2 | 9/2006 | Jaeger et al. |
| 11,207,474 | B2* | 12/2021 | Dunne ................ B05B 11/0054 |
| 2003/0078551 | A1* | 4/2003 | Hochrainer ......... A61M 15/007 |
| | | | 604/295 |
| 2003/0106550 | A1* | 6/2003 | Harvey ................. B65D 83/54 |
| | | | 128/205.24 |
| 2004/0164186 | A1* | 8/2004 | Kladders ........... A61M 15/0065 |
| | | | 239/543 |
| 2005/0252990 | A1 | 11/2005 | Jaeger et al. |
| 2008/0178871 | A1* | 7/2008 | Genova ................ A61M 15/08 |
| | | | 128/200.23 |
| 2010/0199984 | A1* | 8/2010 | Williams, III ....... A61M 11/007 |
| | | | 128/200.23 |
| 2011/0041840 | A1* | 2/2011 | Dunne .................. A61M 11/06 |
| | | | 128/200.14 |
| 2011/0168175 | A1* | 7/2011 | Dunne .................. B65D 83/42 |
| | | | 222/321.6 |
| 2014/0041657 | A1 | 2/2014 | Meyer et al. |
| 2015/0040891 | A1 | 2/2015 | Avni |
| 2015/0320948 | A1* | 11/2015 | Eicher ............... A61M 15/0068 |
| | | | 128/200.21 |

FOREIGN PATENT DOCUMENTS

| | | | | |
|---|---|---|---|---|
| JP | 1992-076975 U1 | 7/1992 | | |
| WO | WO-9007351 A1 * | 7/1990 | ............ | A61M 15/00 |
| WO | WO-2013150129 A1 * | 10/2013 | .......... | A61M 11/007 |
| WO | WO 2014/019563 | 2/2014 | | |

OTHER PUBLICATIONS

English translation for JP1992-076975U1, human translated on Dec. 2021.*
Russian Office Action issued in corresponding Russian Patent Application No. 2019104717, dated Sep. 9, 2020, 9 pages.
International Search Report for International Application No. PCT/EP2017/074775, dated Dec. 20, 2017, 3 pages.
WO2014019563, Chris Aworth, "Nozzle Arrangement," Feb. 6, 2014, English language machine translation of abstract, Espacenet, date obtained: May 31, 2019, 2 pages <URL: https://worldwide.espacenet.com/publicationDetails/biblio?CC=WO&NR=2014019563A1&KC=A1&FT=D&ND=3&date=20140206&DB=&locale=en_EP>.

* cited by examiner

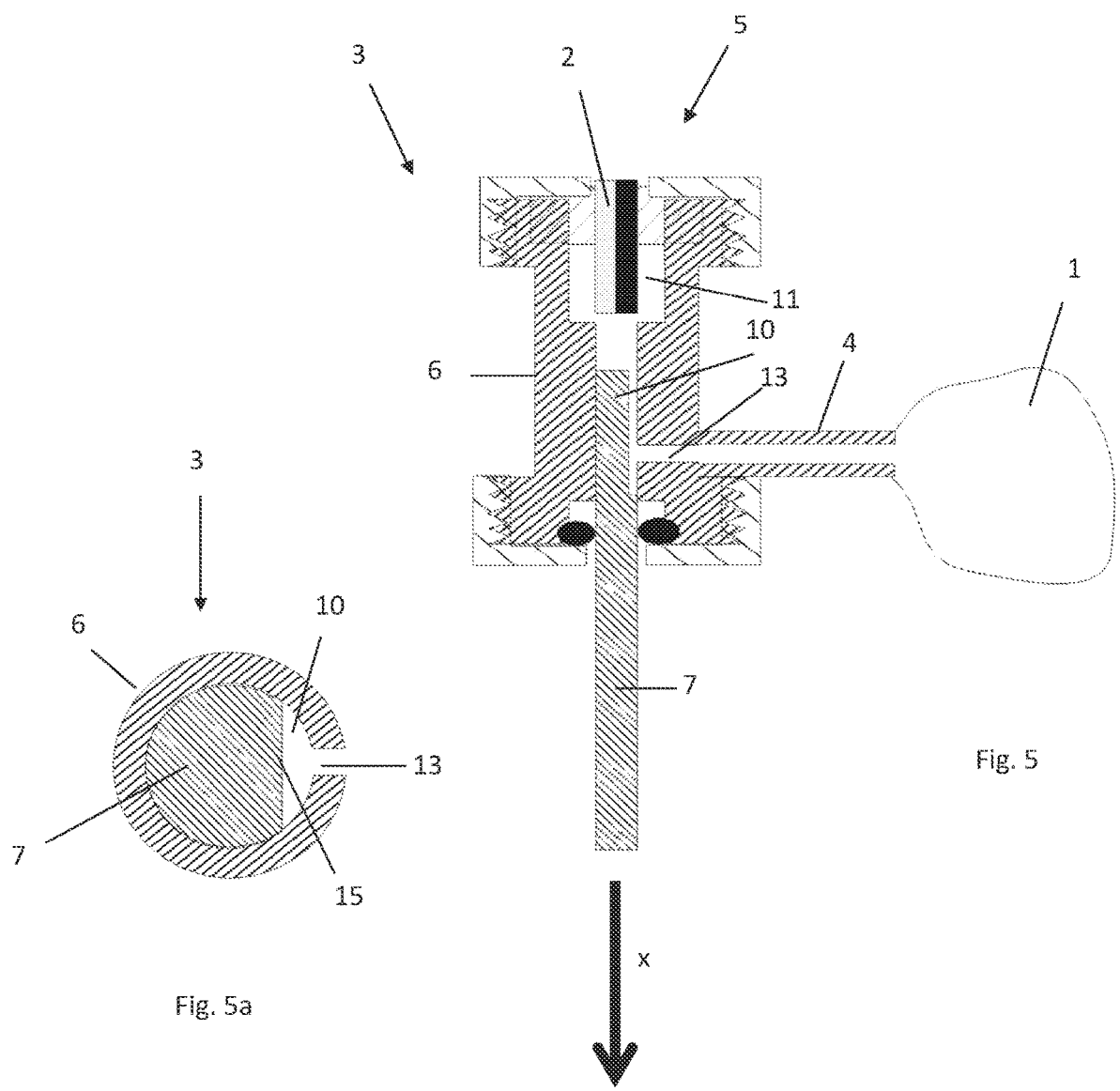

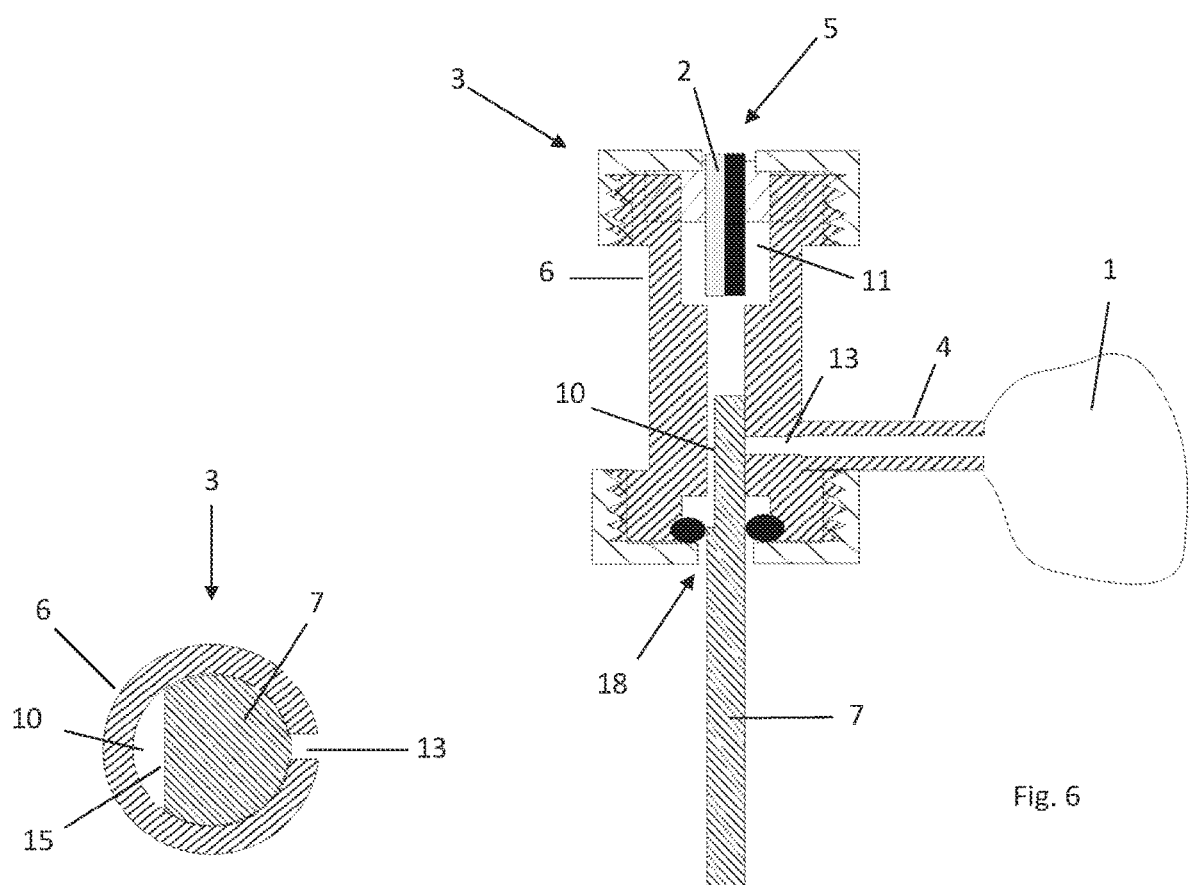

ATOMISER, IN PARTICULAR INHALER, FOR ATOMISING A LIQUID ACTIVE AGENT TO FORM AN AEROSOL AND A CORRESPONDING METHOD

CROSS-REFERENCE TO RELATED APPLICATIONS

This application is a United States Application under 35 U.S.C. § 371 claiming priority to and the benefit of PCT Application No. PCT/EP2017/074775, filed Sep. 29, 2017, which claims priority to and the benefit of German Application No. 10 2016 118 654.6, filed on Sep. 30, 2016, the contents of each of which are hereby incorporated by reference in their entireties.

The invention is based on an atomiser, in particular an inhaler, for atomising a liquid active agent to form an aerosol and on a corresponding method. The atomiser has an active agent reservoir, an atomising nozzle and a pump arrangement, wherein a suction side of the pump arrangement opens out into the active agent reservoir and a pressure side of the pump arrangement into the atomising nozzle. The pump arrangement has a piston that is adjustable in a cylinder in the axial direction of the cylinder. Such an atomiser is known, for example, from U.S. Pat. No. 7,104,470 B2 and from U.S. Pat. No. 5,662,271 A. An exemplary atomising nozzle is known from DE 10 2012 014 965 A1.

With atomisers known from the prior art, an inlet valve is often provided, which seals a pump chamber of the pump arrangement with regards to the active agent reservoir, when an overpressure is generated in the pump chamber for the emission of an aerosol via the atomising nozzle, such that a return flow of the active agent from the pump chamber into the active agent reservoir is avoided. When the pump chamber is to be refilled, a negative pressure is generated in the pump chamber by displacing the piston, whereby the active agent is transported from the active agent reservoir through the open inlet valve into the pump chamber. During the suction process, an outlet valve allocated to the atomising nozzle is sealed in order to avoid a return flow of liquid or air from the atomising nozzle into the pump chamber.

For sucking the active agent from the reservoir, the piston of the pump arrangement is often formed as a capillary or as a hollow piston, having a non-return valve, which serves as a sealing element for the capillary with a ball that is moveable in the capillary, when an overpressure is generated in the pump chamber, in order to emit the aerosol via the atomising nozzle. However, such pump pistons formed as capillaries are laborious in terms of production and, correspondingly, are cost-intensive.

It is thus the object of the invention to further develop an atomiser of the kind described above and a corresponding method in such a way that they are simple and cost-effective in terms of production.

This object is solved by an atomiser having the features of claim 1 and a corresponding method having the features of claim 12. The dependent claims each relate to advantageous embodiments of the invention.

Accordingly, the piston abuts proportionately along the outer periphery of the piston in a positive fitting manner on an inner wall of the cylinder, wherein, furthermore, a gap is proportionately formed between the inner wall of the cylinder and the piston. The piston is rotatably mounted in the cylinder around its longitudinal axis and can be adjusted between a suction position, in which a pump chamber of the pump arrangement is connected to the suction side via the gap, and a pump position, in which the piston seals the suction side.

In comparison to the atomisers known from the prior art, the described embodiment of the pump arrangement enables, in particular, that the piston can be formed as a massive component and must no longer be formed as a capillary with integrated (ball) non-return valve. A massive and integrally formed piston can be achieved during production substantially more simply and thus more cost-effectively than the piston previously described with integrated capillary and ball non-return valve. If the piston abuts on the inner wall of the cylinder in a positive fit manner along the outer periphery, the outer periphery can have an outer diameter which substantially corresponds to an inner diameter of the cylinder. Here, the outer dimeter of the piston can be between 0.1 mm and 3 mm, and particularly preferably between 0.2 and 1 mm. The piston can be guided in the cylinder between the pump position and the suction position along the surfaces of the piston and the cylinder, said surfaces abutting on one another in positive lock manner If the gap is formed between the inner wall of the cylinder and the outer periphery of the piston, the outer periphery of the piston can be non-round and, in particular, have a flattened portion. Here, the piston can be formed, for example, as a round rod, which is flattened on one side on an end, with which it protrudes into the pump chamber, wherein the flattened portion can be formed, for example, by local, lateral material removal, for example by milling of the round rod.

The suction side of the pump arrangement can be connected to the pump chamber via a passage extending in the radial direction of the cylinder and opening out into the gap in the suction position.

Here, an inner shell surface on the inner periphery of the cylinder can have a constant curvature radius over its entire surface and can only be interrupted via the passage. At a transition between the passage and inner wall of the cylinder, a sealing element surrounding the passage can be arranged in order to further improve the sealing of the passage with respect to the pump chamber in the pump position of the piston.

In the suction position, the gap can be facing towards the passage and, in the pump position, facing away from the passage, wherein the suction position and the pump position are two adjustment positions of the piston rotated by substantially 180° in relation to each other. It is not necessarily required for sealing the passage in the pump position that the piston is rotated by 180° in relation to the suction position, in which the gap is facing towards the passage. Depending on the manufacturing tolerance between the outer periphery of the piston and the inner periphery of the cylinder that can be realised and the pressure tightness between passage and pump chamber in the pump position that can be achieved, the pump position can also be rotated by less than 180°, for example by only 90°, in relation to the suction position.

For example, the piston can be a circular cylinder which has a recess on a side running in parallel to the longitudinal axis of the piston. In particular, the piston can be a circular cylinder that is flattened on one side. A connection surface between the circular shell surface of the piston and the recess or a flattened side can be rounded. This embodiment contributes to a sealing element that is potentially provided and which surrounds the passage on the inner wall of the cylinder not being damaged during the rotation of the piston between the suction position and the pump position. According to a different aspect, the invention relates to a method for the operation of an atomiser of the kind described above. The method includes shifting the piston in relation to the cylinder in the longitudinal direction of piston and cylinder between an extended position and an inserted position.

Here, it can be provided that, when shifting the piston from the extended position into the inserted position of the piston, the suction side is sealed, whereas, when shifting the piston from the inserted position into the extended position, the gap connects the suction side to the pump chamber.

For sealing the suction side, the piston can be rotated about its longitudinal axis from the suction position into the pump position.

Furthermore, the method can include the following steps:
a) shifting the piston along its longitudinal direction from the inserted position into the extended position, wherein the piston is in the suction position, and wherein a negative pressure is generated in the pump chamber, such that a liquid active agent is drawn from the active agent reservoir into the pump chamber, then
b) rotating the piston from the suction position into the pump position; then
c) shifting the piston from the extended position into the inserted position, wherein a negative pressure is generated in the pump chamber, and the liquid active agent in the pump chamber is emitted from the atomiser via the atomising nozzle; then
d) rotating the piston from the pump position into the suction position.

In order to emit further aerosol, steps a) to d) can be repeated at least once, corresponding to the desired amount of aerosol.

DESCRIPTION OF THE FIGURES

Further details of the invention are explained by means of the figures below. Here are shown:

FIGS. 3 to 6 schematically, an embodiment of the atomiser according to the invention in various adjustment positions of the piston in relation to the cylinder.

FIG. 1 shows an atomiser according to the prior art. This substantially consists of an active agent reservoir 1 and an atomising nozzle 2, which are fluidically connected to each other via a pump arrangement 3. An active agent stored in the active agent reservoir 1 can be pressed through the atomising nozzle 2 via the pump arrangement 3 under pressure, such that it is atomised in the finest particles and forms an aerosol. A suitable atomising nozzle is described in DE 10 2012 014 965 A1. The atomiser can be used, for example, as an inhaler.

Figure 1:
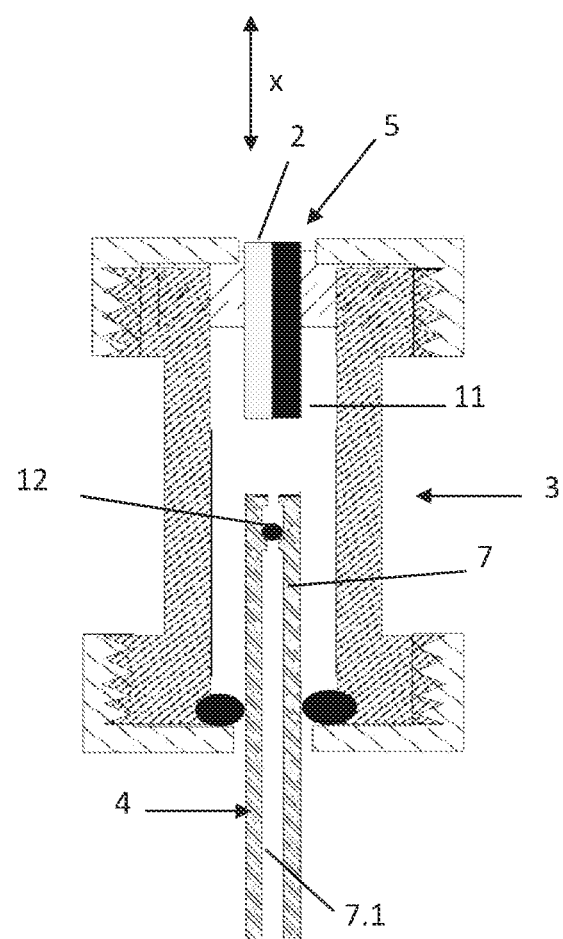
FIG. 1 an atomiser according to the prior art.

The pump arrangement 3 has a suction side 4 and a pressure side 5, wherein the suction side is fluidically connected to the active agent reservoir 1 via a capillary 7.1 in a piston 7 of the pump arrangement 3. Furthermore, the pump chamber 11 is fluidically connected to the atomising nozzle 2.

The piston 7 can be shifted in the cylinder 6 in its longitudinal direction x. On its end protruding into the pump chamber 11, the piston 7 has a ball valve 12, which releases the capillary 7.1 when the piston 7 is at least partially pulled out of the pump chamber 11 in a suction movement, and that the capillary 7.1 seals when the piston 7 is inserted further into the pump chamber 1 in a pump movement. Thus, when the piston 7 is at least partially pulled out of the pump chamber 11, an active agent can emerge out of the active agent reservoir 1 through the capillary 7.1 into the pump chamber 11 as a result of the negative pressure occurring in the pump chamber 11.

Then, when the piston 7 is further reinserted into the pump chamber 11 in a following step, the ball valve seals the capillary 7.1 because of the overpressure emerging here in the pump chamber 11, such that the active agent in the pump chamber 11 only emerges from the pump chamber 11 via the atomising nozzle 2 and, in particular, cannot flow back into the active agent reservoir 1 through the capillary 7.1.

In the region of the active agent atomiser, the pistons 7 usually have a diameter of roughly 0.9 to 1.5 mm, such that the capillary extending inside the piston 7 in the longitudinal direction of the piston must have a correspondingly smaller diameter. Here, the formation of the ball non-return valve 12, in particular, is highly complex, wherein production tolerances must be maintained in the micrometre range to ensure the functional efficiency of the valve 12, whereby the atomiser is very laborious in terms of production and thus cost-intensive.

Figure 2:
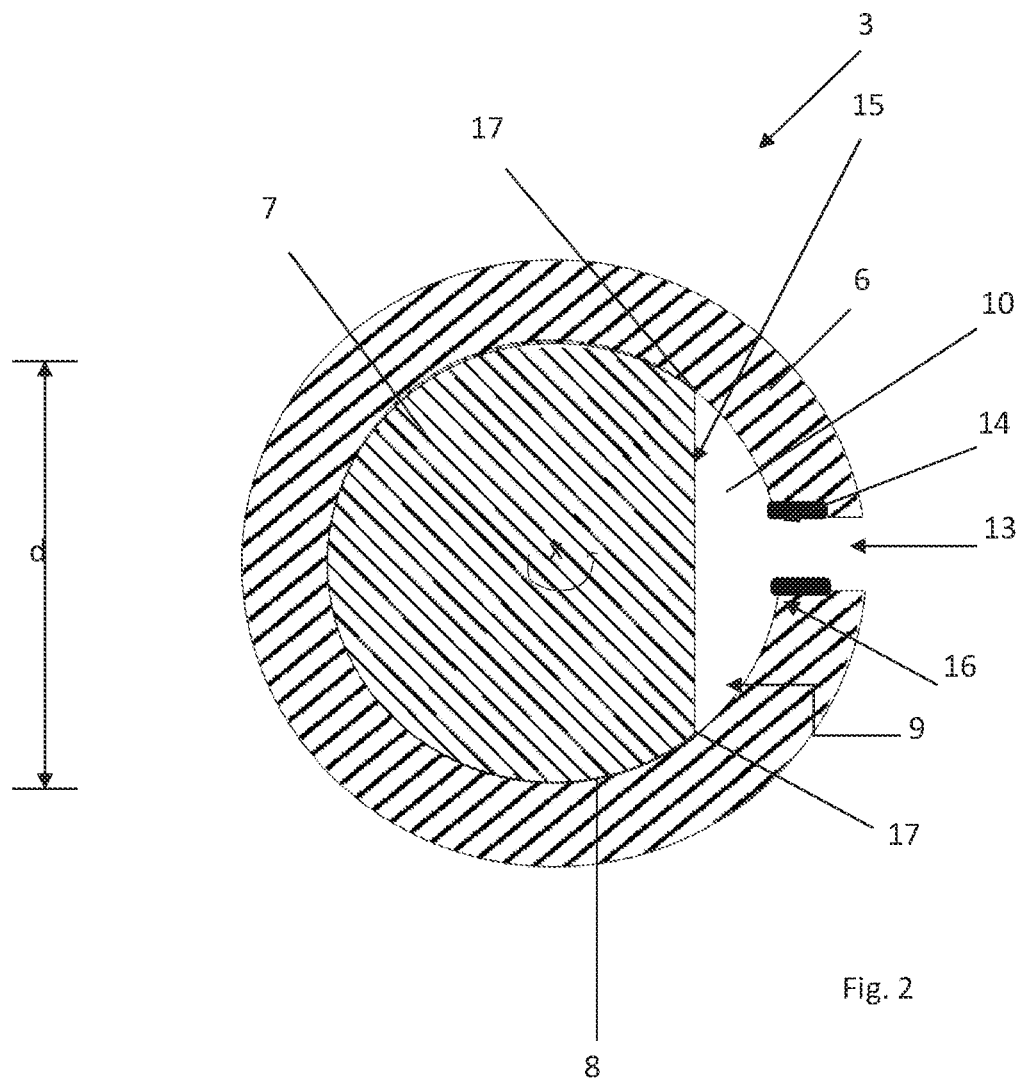
FIG. 2 a schematic cross-sectional view perpendicular to the longitudinal axis of a pump arrangement of an embodiment of an atomiser according to the invention.

In FIG. 2, a cross-section perpendicular to the longitudinal direction of the piston 7 and the cylinder 6 of a pump arrangement 3 is shown according to an embodiment of the invention. Accordingly, the piston has a recess 10 along its outer periphery 8, such that the piston proportionately abuts on the inner wall 9 of the cylinder 6 along its outer periphery 8 in a positive fitting manner and proportionately forms a gap 10 between the inner wall 9 of the cylinder and the piston 7. The piston 7 is rotatably mounted in the cylinder 6 around its longitudinal axis x, which extends perpendicular to the drawing plane in the depiction according to FIG. 2. In FIG. 2, the piston 7 is arranged in the suction position in relation to the cylinder 6. In the suction position, the gap 10 is facing towards a side of the cylinder 6 through which a passage 13 extends in the radial direction of the cylinder 6. The suction side 4 of the pump arrangement 3 can be attached via the passage 13, such that a fluidic connection between an active agent reservoir 1 attached via the suction side 4 and a pump chamber 11 of the pump arrangement 3 can be produced via the passage 13 and the gap 10 (not depicted in FIG. 2, see FIGS. 3 to 6).

The piston 7 can be rotated about its longitudinal axis x running perpendicular to the drawing plan of FIG. 2. When the piston 7 is rotated about the axis x, for example by 180°, in relation to the position shown in FIG. 2, the gap 10 is facing towards a side wall section of the cylinder 6 facing away from the passage 13. In this case, the cylinder 7 seals the passage 13 with its outer periphery abutting on the recess 15.

In order to improve the seal between the inner periphery 9 of the cylinder 6 and the outer periphery 8 of the piston 7 in the region of the passage 13, the passage 13 has a sealing element 14 on its transition to the inner wall 9 of the cylinder 6. By the sealing element 14 not being damaged by the rotation of the piston 7 inside the cylinder 6, the connection surfaces 17, which connect the circular-symmetrical outer periphery 8 of the piston to the recess 5, each have a rounded part.

The recess 15 forming the gap 10 between the piston 7 and the inner wall 9 of the cylinder 6 is formed as a lateral flattened portion of the otherwise substantially circular-cylindrical piston 7.

Figures 3, 3A:
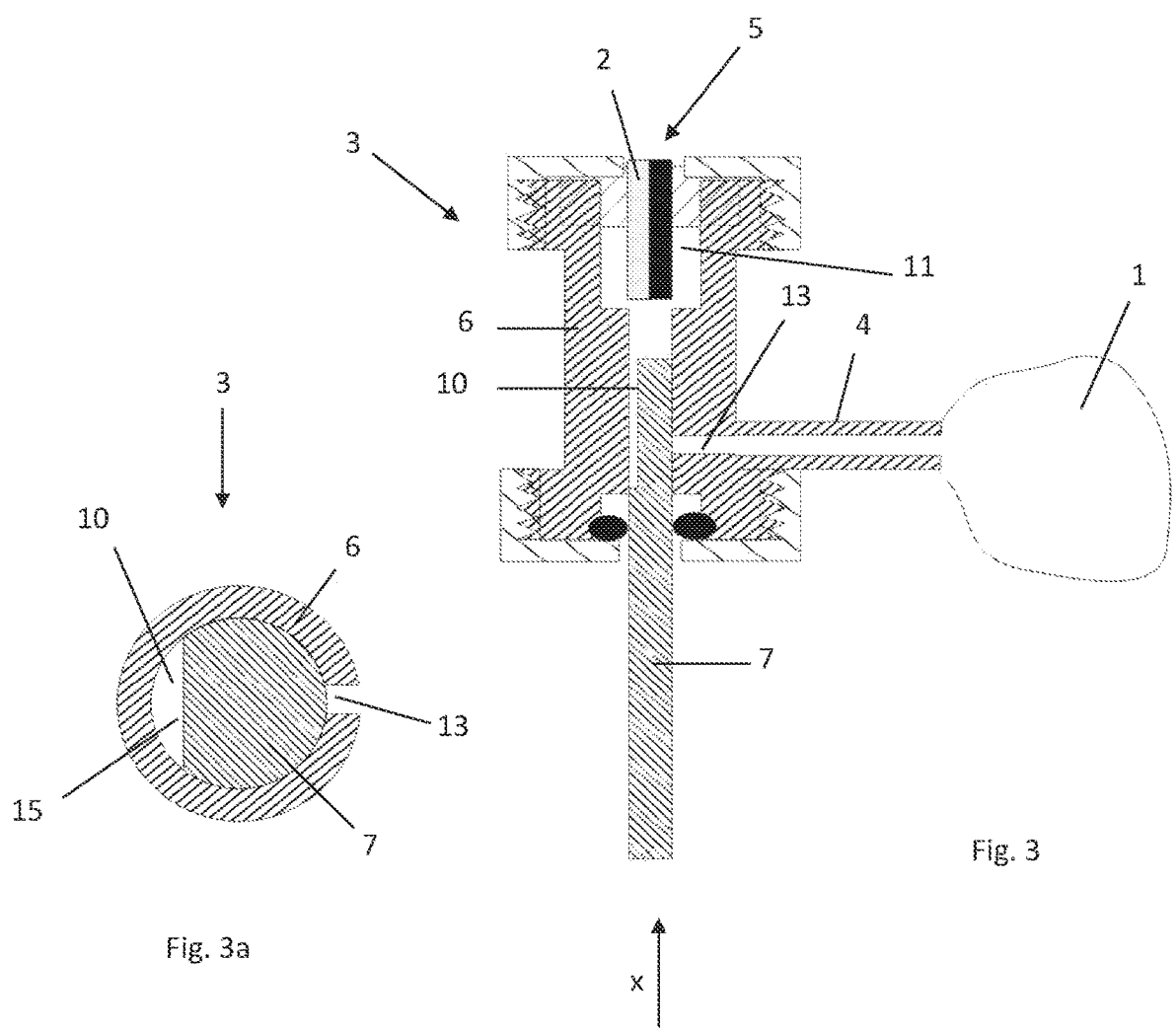

FIGS. 3 to 6 show four different adjustment positions of the piston 7 in relation to the cylinder 6. In FIGS. 3 and 3a, the gap 10 is arranged facing away from the passage 13, such that the piston 7 seals the passage 13. Furthermore, the piston 7 is displaced along its longitudinal axis x from an extended position into an inserted position. Since the piston 7 seals the passage 13, an overpressure can be generated in the pump chamber 11, such that a liquid active agent in the pump chamber is emitted from the atomiser via the atomising nozzle 2.

Figures 4, 4A:
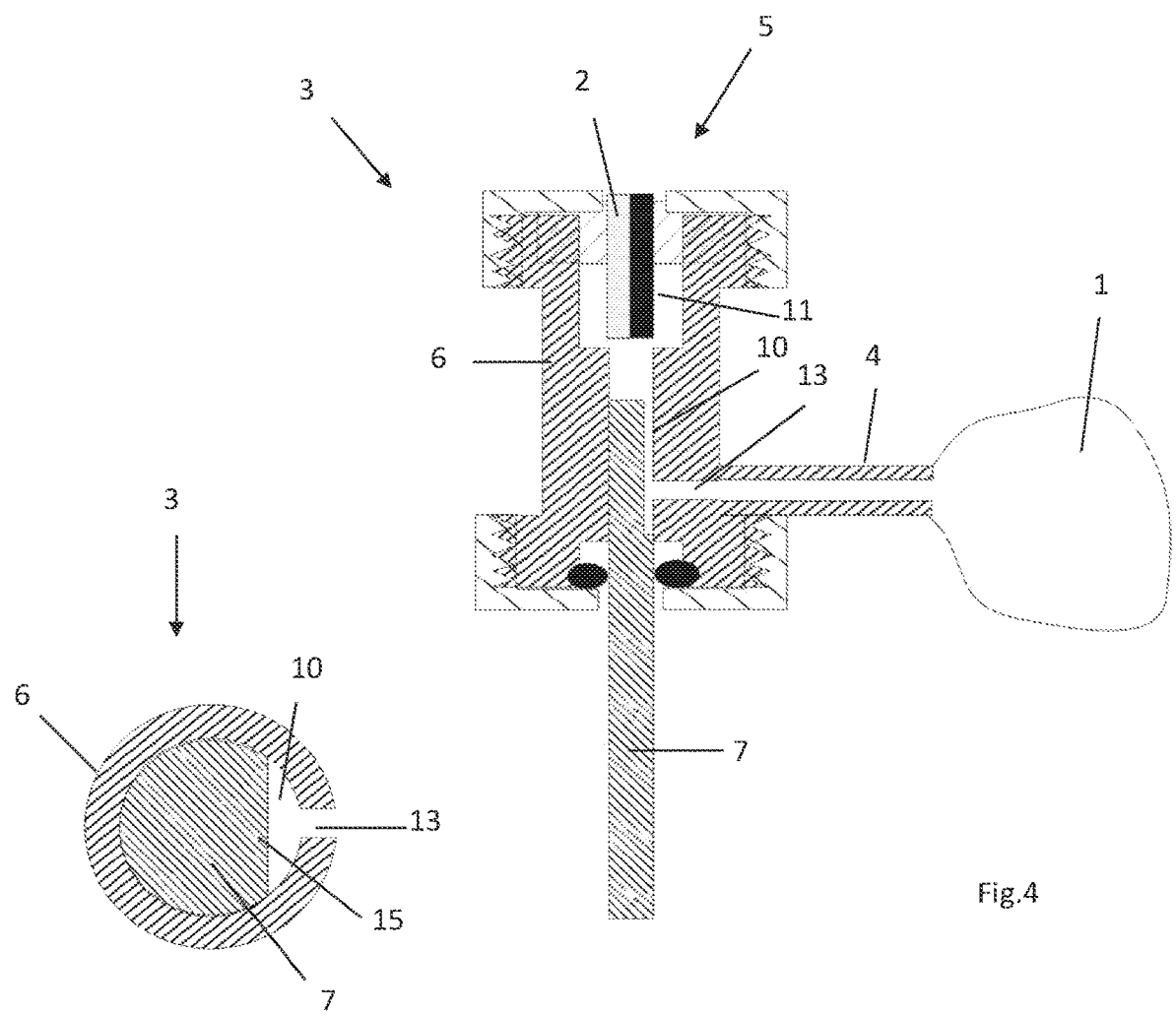

When the piston 7 is in the inserted position, the piston, as is depicted in FIGS. 4 and 4a, is rotated from the pump position shown in FIGS. 3 and 3a into the suction position shown in FIGS. 4 and 4a, in which the gap 10 is facing towards the passage 13, and thus a fluidic connection between the pump chamber 11 and the active agent reservoir 1 is produced via the gap 10, the passage 13 and the suction side 4. In this rotational alignment of the piston 7 in relation to the cylinder 6, the piston 7 can be at least partially drawn out of the pump chamber 11 to fill the pump chamber 11, such that a negative pressure emerges in the pump chamber 11. This is shown in FIGS. 5 and 5a. Because of the negative pressure, an active agent in the active agent reservoir 1 can be conveyed into the pump chamber 11 via the suction side 4, the passage 13 and the gap 10. To do so, the atomising nozzle 2 can have a non-return valve, which seals the nozzle 2 with respect to the outer surroundings of the pump arrangement 3 in the event of a negative pressure in the pump chamber 11.

After the pump chamber 11 has been at least partially filled with active agent, the piston 7 is rotated again in the cylinder 6 by 180°, such that the piston 7 seals the passage 13 in the cylinder.

The pump arrangement 3 is thus prepared to generate an overpressure in the pump chamber 11 corresponding to the situation shown in FIGS. 3 and 3a, by renewed displacement of the piston 7 along the longitudinal direction x from the extended position into the inserted position, such that further liquid active agent is emitted from the atomiser via the atomising nozzle 2.

In the embodiments shown in FIGS. 2 to 6a, the piston 7 is formed as a circular cylinder flattened on one side in cross-section perpendicular to the longitudinal direction of the piston and thus, by one-sided, sectional flattening of a circular cylindrical piston, can be produced simply and thus cost-effectively. Furthermore, it is to be recognised that the recess 15 is only formed on the end of the piston 7 protruding into the pump chamber 11, wherein the piston is circular symmetrical in cross-section perpendicular to its longitudinal axis, in particular, in a sealing region 18, in which the piston 7 is sealed to the pump chamber 11, such that the piston 7 can be sealed to the pump chamber 11 with a simple sealant, for example with an O-ring.

The features of the invention disclosed in the description above, in the drawings and in the claims can be substantial both individually and in any combination for the realisation of the invention.

LIST OF REFERENCE NUMERALS

1 Active agent reservoir
2 Atomising nozzle
3 Pump arrangement
4 Suction side of the pump arrangement
5 Pressure side of the pump arrangement
6 Cylinder
7 Piston
7.1 Capillary
8 Outer periphery
9 Inner wall
10 Gap
11 Pump chamber
12 Ball valve
13 Passage
14 Sealing element
15 Recess
16 Transition
17 Connection surface
18 Sealing region
d Outer diameter of the piston
x Longitudinal axis

The invention claimed is:

1. An inhaler, for atomising a liquid active agent to form an aerosol, having an active agent reservoir, an atomising nozzle and a pump arrangement, wherein a suction side of the pump arrangement opens out into the active agent reservoir and a pressure side of the pump arrangement into the atomising nozzle, and wherein the pump arrangement has a piston that is capable of being adjusted in a cylinder in an axial direction of the cylinder, wherein the piston abuts proportionately on an inner wall of the cylinder in a positive fitting manner along an outer periphery of the piston, and a gap is formed proportionately between the inner wall of the cylinder and the piston, wherein the piston is rotatably mounted around a longitudinal axis of the piston in the cylinder and is capable of being adjusted between a suction position, in which a pump chamber of the pump arrangement is connected to the suction side via the gap, and a pump position, in which the piston seals the suction side.

2. An inhaler according to claim 1, in which the piston is integrally formed.

3. An inhaler according to claim 1, in which the piston is configured to abut on the inner wall of the cylinder in a positive fitting manner along the outer periphery, the outer periphery of the piston has an outer diameter, which substantially corresponds to an inner diameter of the cylinder.

4. An inhaler according to claim 3, wherein the outer diameter of the piston is between 0.1 mm and 3 mm.

5. An inhaler according to claim 3, wherein the outer diameter of the piston is between 0.2 mm and 1 mm.

6. An inhaler according to claim 1, in which the gap is configured to be formed between the inner wall of the cylinder and the outer periphery of the piston, and in which the outer periphery of the piston is non-round.

7. An inhaler according to claim 6, wherein the outer periphery of the piston is non-round and flattened.

8. An inhaler according to claim 1, in which the suction side of the pump arrangement is connected to the pump chamber via a passage extending in a radial direction of the cylinder and opening out into the gap in the suction position.

9. An inhaler according to claim 8, in which an inner shell surface has a constant curvature radius on an inner periphery of the cylinder across an entire surface of the inner shell surface and is only interrupted via the passage.

10. An inhaler according to claim 8, in which a sealing element surrounding the passage is arranged on a transition between the passage and the inner wall of the cylinder.

11. An inhaler according to claim 8, in which, in the suction position, the gap is facing towards the passage and, in the pump position, is facing away from the passage, wherein the suction position and the pump position are two adjustment positions of the piston that are substantially rotated in relation to each other by 180°.

12. An inhaler according to claim 1, in which the piston is a circular cylinder which has a recess on a side running in parallel to the longitudinal axis of the piston.

13. An inhaler according to claim 12, in which the piston is a circular cylinder flattened on one side.

14. An inhaler according to claim 13, in which a connection surface between a circular surface of the piston and the recess or the flattened side is rounded.

15. A method for atomizing the liquid in the inhaler according to claim 1, that includes the step of shifting the piston in relation to the cylinder in the longitudinal direction of the piston and the cylinder from an extended position to an inserted position.

16. A method according to claim 15, in which, during the shifting of the piston from the extended position to the inserted position, the piston seals the suction side, and in which, during the shifting of the piston from the inserted position to the extended position, the gap connects the suction side to the pump chamber.

17. A method according to claim 15, in which the piston is rotated about the longitudinal axis of the piston from the suction position into the pump position for sealing the suction side.

18. A method according to claim 15, which has the following steps:
- a) shifting the piston along the longitudinal direction of the piston from the inserted position to the extended position, wherein the piston is in the suction position and wherein a negative pressure is generated in the pump chamber, such that a liquid active agent is drawn out of the active agent reservoir into the pump chamber, then
- b) rotating the piston out of the suction position into the pump position; then
- c) shifting the piston from the extended position to the inserted position, wherein the piston is furthermore in the pump position, and wherein a positive pressure is generated in the pump chamber, and the liquid active agent in the pump chamber is emitted out of the inhaler via the atomising nozzle; then
- d) rotating the piston out of the pump position into the suction position;
- e) selectively repeating steps a) to d).

\* \* \* \* \*